United States Patent [19]

Zweig

[11] Patent Number: 4,974,249
[45] Date of Patent: Nov. 27, 1990

[54] X-RAY INSPECTION SYSTEM

[75] Inventor: Gilbert Zweig, Morris Plains, N.J.

[73] Assignee: Glenbrook Technologies, Inc., Victory Gardens, N.J.

[21] Appl. No.: 360,461

[22] Filed: Jun. 2, 1989

[51] Int. Cl.⁵ .............................. G21K 4/00
[52] U.S. Cl. .................... 378/190; 378/62; 378/189; 378/208
[58] Field of Search ............ 378/41, 42, 62, 63, 378/99, 189–190, 195, 208, 209

[56] References Cited

U.S. PATENT DOCUMENTS

| | | | |
|---|---|---|---|
| 2,041,682 | 5/1936 | Adrian | 378/192 |
| 2,298,942 | 10/1942 | Hicks et al. | 378/190 |
| 2,683,812 | 7/1954 | Schneeman | 378/190 |
| 3,344,276 | 9/1967 | Balding | 378/190 |
| 3,488,495 | 6/1970 | Schneeman | 378/69 |
| 3,499,150 | 3/1970 | Tajima et al. | 378/62 |
| 3,573,455 | 4/1971 | Suierveld | 378/58 |
| 3,612,867 | 10/1971 | Rabodzei et al. | 378/189 |
| 3,614,427 | 10/1971 | Vacher | 378/189 |
| 3,636,351 | 1/1972 | Lajus | 378/171 |
| 3,678,278 | 7/1972 | Peil | 378/62 |
| 3,679,901 | 7/1972 | Bogren et al. | 378/63 |
| 3,790,785 | 2/1974 | Paolini et al. | 378/99 |
| 3,824,399 | 7/1974 | Bjork et al. | 378/99 |
| 3,860,819 | 1/1975 | Rabodzei et al. | 378/189 |
| 4,142,101 | 2/1979 | Yin | 250/483 |
| 4,379,348 | 4/1983 | Haas et al. | 378/190 |
| 4,587,555 | 6/1986 | Carollo et al. | 358/111 |
| 4,736,397 | 4/1988 | Valasquez | 378/99 |
| 4,803,639 | 2/1989 | Steele et al. | 364/507 |

OTHER PUBLICATIONS

Abstract of Jap. Appl. 60-260806A, Dec. 24, 1985, K. Tanaka.

Primary Examiner—Janice A. Howell
Assistant Examiner—John C. Freeman
Attorney, Agent, or Firm—Birch, Stewart, Kolasch & Birch

[57] ABSTRACT

A high resolution X-ray inspection system particularly adapted for electronic circuit components comprised of an X-ray cabinet including an X-ray tube which is located in a vertical tower and where the object and film are placed on a slidable support member located inside the lower portion of the cabinet, with the support member being slidable outwardly therefrom. The slidable support member includes provision for attaching, upon demand, a fluoroscopic imaging device whose output is optically coupled to a closed circuit TV camera located in the bottom of the housing beneath the slidable shelf. The fluoroscopic generator includes a thinly coated radioluminescent phosphor plate optically coupled to the input of an image intensifier comprised of a microchannel plate multiplier.

18 Claims, 1 Drawing Sheet

X-RAY INSPECTION SYSTEM

BACKGROUND OF THE INVENTION

This invention relates generally to X-ray imaging apparatus and more particularly to an industrial X-ray inspection system capable of providing both film and high resolution fluoroscopic images of objects under inspection.

Industrial X-ray inspection systems are generally well known and are used for the non-destructive examination of objects such as castings, electronic components and assemblies as well as biological samples. Such apparatus include cabinets comprised of lead lined steel structures including a generally vertical tower assembly having an X-ray tube located at the top thereof. During an inspection procedure, a piece of X-ray film is normally placed on a shelf in the cabinet at the bottom of the tower and the object of interest is placed on top of the film. Such industrial X-ray systems also typically include means to adjust the voltage and exposure time to achieve optimum image contrast of the film image. The object is then exposed to X-rays which pass through the object to produce a shadowgraph on the X-ray film which becomes visible to the eye when developed. Such apparatus is similar in many respects to that utilized for medical procedures.

As in the case of medical X-ray examination systems, X-ray inspection systems used for industrial applications also utilize systems which provide fluoroscopic or "real time" imaging. These systems also employ X-ray tubes; however, instead of recording the X-ray image on film, the X-ray image is converted to a video image which is viewed via closed circuit television apparatus. In some such systems, a videcon tube converts the X-ray image directly into a video image which is displayed. Vidicon sensitive X-ray cameras, however, are expensive and short lived. In others, the X-ray image is converted to a visible image by a cesium iodide image intensifier for video viewing. Such apparatus is large and very expensive. One known type of image intensifier which has become extremely useful includes a thin coating of radioluminescent phosphor which is coupled to the input of a microchannel plate type image intensifier whose output is fed to a phosphor for generating a visible image which can thereafter be viewed. This type of apparatus is smaller in size and less costly than the above mentioned types.

SUMMARY

It is an object of the present invention, therefore, to provide an improvement in X-ray imaging apparatus.

It is another object of the invention to provide an improvement in X-ray inspection apparatus.

It is a further object of the invention to provide a high resolution industrial X-ray inspection system suitable for inspecting electronic components including circuit boards therefor.

And still yet another object of the invention is to provide an improvement in an industrial X-ray inspection system which is capable of providing both film images as well as fluoroscopic images of electronic components and assemblies therefor.

And still another object of the invention is to provide an improved X-ray cabinet for an industrial X-ray inspection system which is capable of easily being retrofitted to include a real time or fluoroscopic capability along with a pre-existing X-ray film capability.

Yet a further object of the invention is to provide an X-ray inspection system structure for both film and real time displays having inherently lower cost than any currently available.

Briefly, the foregoing and other objects of the invention are achieved by a high resolution X-ray inspection system particularly adapted for electronic circuit components comprised of an X-ray cabinet including an X-ray tube which is located in a vertical tower and where the object and film are placed on a slidable support member such as a shelf or drawer located inside the lower portion of the cabinet, with the shelf or drawer being slidable outwardly therefrom. The support member has provision for a fluoroscopic imaging device which can be fitted thereto upon demand or it can be mounted in the bottom of the cabinet apart from the support member. The output of the fluoroscopic imaging device is optically coupled to a closed circuit TV camera located in the bottom of the housing beneath the slidable shelf. The fluoroscopic imaging device is comprised of a thinly coated radioluminescent phosphor plate optically coupled to the input of an image intensifier including a microchannel plate multiplier. The fluoroscopic TV image generated is viewed on a monitor located, for example, adjacent the X-ray cabinet.

BRIEF DESCRIPTION OF THE DRAWING

The foregoing and other objects of the invention will be more readily understood when the followed detailed specification is considered together with the drawing in which.

DETAILED DESCRIPTION OF THE INVENTION

Figure 1:
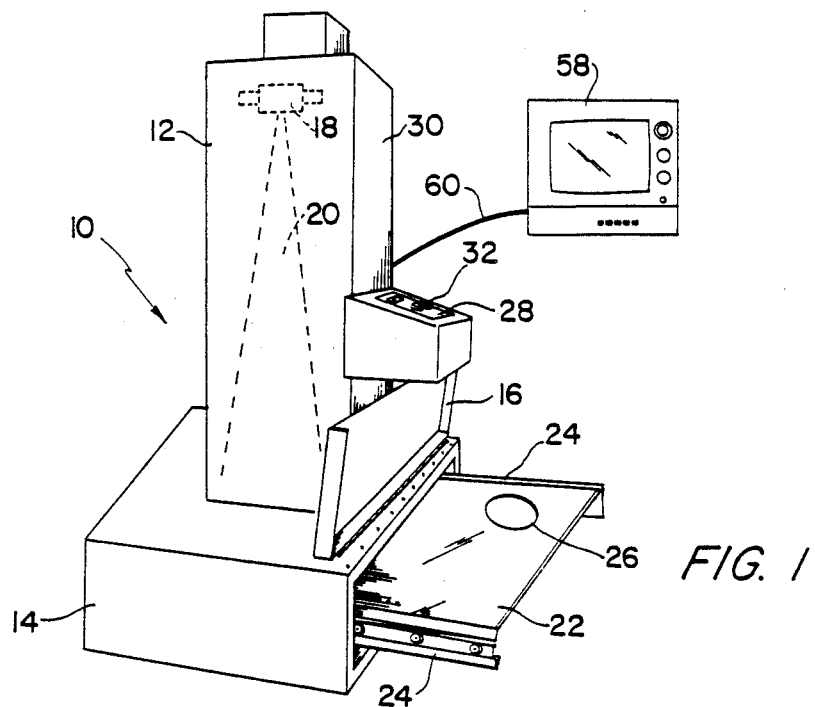
FIG. 1 is a perspective view generally illustrative of the preferred embodiment of the invention.

Referring now to the drawing and more particularly to FIG. 1, reference numeral 10 denotes an X-ray cabinet for an X-ray inspection system for industrial applications and utilized, for example, in the inspection of electronic components and circuit boards therefor, castings and, when desirable, even biological specimens.

The X-ray cabinet 10 is comprised of a lead lined steel structure including a generally vertical tower, typically having a height, for example, of 31 inches which sits above an inspection chamber or housing 14. The tower 12 contains an X-ray tube in the top portion thereof which generates a collimated X-ray beam 20. The beam 20 is directed downwardly into the top of the inspection chamber 14 as shown in FIG. 2.

A slide-out support member 22 comprised of a drawer or shelf is mounted generally horizontally within the inspection chamber 14 by means of a slide rail assembly, or the like, 24 so that it can be manually moved back and forth for the loading and unloading of objects, not shown, to be inspected. As shown, a hinged door 16 is adapted to close the front of inspection chamber 14. When desirable, however, this could be deleted in favor of a flat vertical panel or front piece attached to the support member. The shelf 22 includes a generally flat top surface where X-ray film can be placed beneath the object to be inspected during a routine shadowgraph imaging mode in a well known manner. The shelf 22, moreover, includes an aperture 26 therethrough, shown in FIG. 1 as being a generally circular opening for the location of apparatus for performing "real time" or fluoroscopic inspection as will be explained hereinater. The aperture 26, however, can be completely eliminated, if desired, as long as this particular area of the shelf or the whole shelf member 22 is completely X-ray transparent.

Additionally, the X-ray cabinet 10 has a control panel 28 mounted on the front side wall 30 of the tower 12 and includes one or more manually operable devices 32 for controlling the X-ray tube 18 in a well known manner for performing both filming and fluoroscopic inspection of objects placed on the shelf 22. This configuration provides a compact X-ray cabinet structure which has particular utility for the X-ray inspection of multi-layer printed circuit boards including the multi-layer lamination registration thereof, drilling registration and failure analysis thereof including both populated and unpopulated boards.

Figure 2:
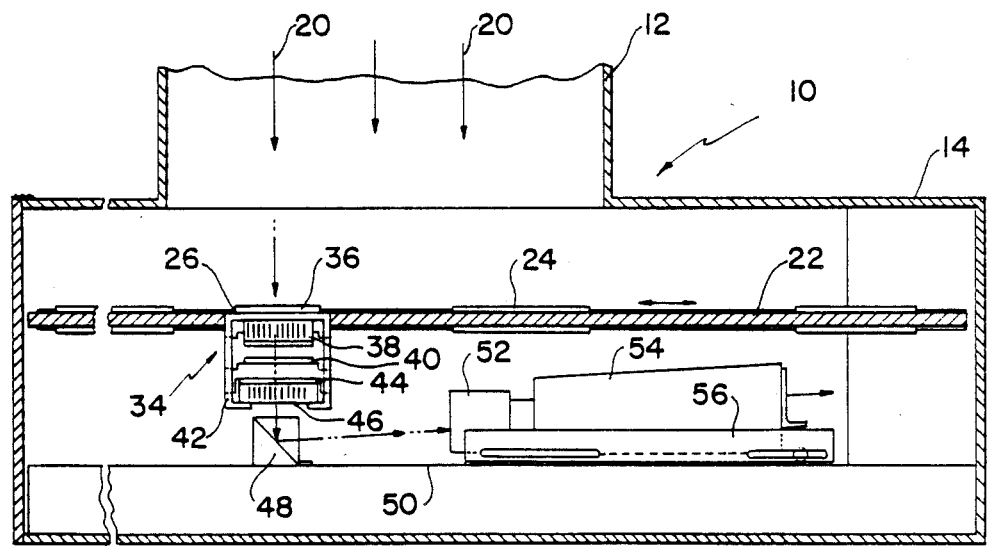
FIG. 2 is a partial transverse vertical section of the lower portion of the embodiment shown in FIG. 1.

Because printed circuit board and electronic fabrication requires rapid X-ray inspection cabability with good resolution, the present invention contemplates providing, during either original equipment manufacture or at a later date, as a retrofit either in the factory or on site, the inclusion of a microchannel plate image intensifier 34 which, as shown in FIG. 2, is mounted on the underside of the shelf 22 at the location of the opening 26. The device 34 includes an X-ray phosphor element 36 coupled to a fiber optic face plate 38 located adjacent a microchannel plate multiplier 40 within a housing element 42. The housing element 42 also includes a visible light phosphor element 44 positioned between the microchannel plate 40 and a fiber optic output face plate 46. The microchannel plate device 34 comprises a well known X-ray imaging device of the type disclosed, for example, in U.S. Pat. No. 4,142,101, issued to L.I. Yin on Feb. 27, 1979. It is also available commercially as a Model 3603-2 microchannel plate image intensifier from the Varo Corporation. What is necessary, however, is that the phosphor element 36 be sufficiently thin in coating thickness so that it is capable of producing a light image of high resolution. The microchannel plate multiplier 40, however, amplifies the light energy so that it can be utilized in connection with a closed circuit TV camera.

Accordingly, and as shown in FIG. 2, the output of the image intensifier device 34 is directed to an aluminized prism or mirror 48 located directly beneath the image intensifier device 34 on a flat base 50 located at the bottom of the inspection housing 14. The visible image is reflected from the prism 48 and directed to the lens 52 of a closed circuit TV camera 54 mounted on a support bracket 56 secured to the base 50. The video output from the camera 54 is coupled to a monitor 58 by means of a cable 60 as shown in FIG. 1 where the object under inspection can be viewed in real time. When desirable, the image intensifier device 34 can be detached from the underside of the shelf 22 and secured directly on the surface of the base 50 over the prism 48.

Thus the microchannel plate image intensifier embodiment of the subject invention provides a high resolution image which can be displayed. The image intensifier, moreover, is compact and can be powered by batteries which can be attached to the sliding shelf 22 without restraining it or requiring any physical or electrical connection to the base 50. The overall combination of elements results in a relatively low cost and compact multi-function, i.e. both film and real time capability, industrial X-ray system available with resolution suitable for MLB inspection.

Having thus shown and described what is at present considered to be the preferred embodiment of the invention, it should be noted that the same has been made by way of illustration and not limitation. Accordingly, all modifications, alterations and changes coming within the spirit and scope of the invention are herein meant to be included.

I claim:

1. An X-ray inspection system, comprising:
   a shield X-ray cabinet including an X-ray exposure chamber providing for the passage of an X-ray beam thereto,
   said exposure chamber having a slidable support member separating an upper portion and a lower portion thereof, said upper portion receiving said X-ray beam from an overhead X-ray source, said support member further having a top and bottom surface, said top surface facing said X-ray source and acting as a surface for the placement of objects to be inspected thereon during either an X-ray filming procedure or a real time fluoroscopic inspection procedure, said slidable support member including an aperture to the lower portion of said exposure chamber;
   fluoroscopic imaging means attached to said slidable support member at said aperture for generating a visible image of an object placed on the surface of said support member and over said fluoroscopic imaging means, said imaging means including radioluminescent phosphor means for converting an X-ray image of said object to a visible image and image intensifier means coupled to said phosphor means and further including a microchannel plate multiplier for providing a relatively high resolution visible image of said object;
   video camera means located in said exposure chamber;
   optical coupling means for coupling the visible image from said fluoroscopic imaging means to said video camera means; and
   a video monitor located externally of said exposure chamber for viewing said object in real time during a fluoroscopic inspection procedure.

2. The X-ray inspection system as defined by claim 1 wherein said fluoroscopic imaging means is attached to the bottom surface of said slidable support member.

3. The X-ray inspection system as defined by claim 2 wherein said radioluminescent phosphor element comprises a relatively thin coated phosphor plate optically coupled to said microchannel plate multiplier.

4. The X-ray inspection system as defined by claim 3 wherein said video camera means and said optical coupling means are located in the lower portion of the exposure chamber.

5. The X-ray inspection system as defined by claim 4 wherein said optical coupling means comprises image reflector means located directly beneath said fluoroscopic imaging means.

6. The X-ray inspection system as defined by claim 5 wherein said exposure chamber includes a generally flat base located in said lower portion thereof and wherein said video camera means and said image reflector means are mounted on said base.

7. The X-ray inspection system as defined by claim 6 wherein said image reflector means comprises a prism or mirror.

8. The X-ray inspection system as defined by claim 1 and additionally including means for controlling the energization of an X-ray tube.

9. The X-ray inspection system as defined by claim 8 wherein said means for controlling includes a control panel located on said X-ray cabinet.

10. The X-ray inspection system as defined by claim 1 wherein said support member comprises a generally flat slidable member having a generally horizontal upper support surface.

11. The X-ray inspection system as defined by claim 10 wherein said support member is comprised of X-ray transparent material.

12. The X-ray inspection system as defined by claim 10 wherein said exposure chamber includes a front opening therein for the withdrawal of said slidable support member from said exposure chamber and additionally including means for closing said opening when said support member is returned to the exposure chamber during an inspection procedure.

13. An X-ray inspection system, comprising:
a shielded X-ray cabinet including an X-ray exposure chamber providing for the passage of an X-ray beam thereto,
said exposure chamber including a support member separating an upper portion and a lower portion thereof, said upper portion receiving said X-ray beam from an overhead X-ray source, said support member further having a top and bottom surface and an aperture therethrough, said top surface facing said X-ray source and acting as a surface for the placement of objects to be inspected thereon during either an X-ray filming procedure or a real time fluoroscopic inspection procedure;
fluoroscopic imaging means located under said support member at said aperture for generating a visible image of an object placed on the top surface of said support member and over said fluoroscopic imaging means, said imaging means including a relatively thin coated phosphor plate for converting an X-ray image of said object to a visible image and image intensifier means coupled to said phosphor plate and further including a microchannel plate multiplier for providing a relatively high resolution visible image of said object;
video camera means located in said lower portion of said exposure chamber;
optical coupling means for coupling the visible image from said fluoroscopic imaging means to said video camera means; and
a video monitor located externally of said exposure chamber for viewing said object in rear time during a fluoroscopic inspection procedure.

14. The X-ray inspection system as defined by claim 13 wherein said optical coupling means are located in the lower portion of the exposure chamber.

15. The X-ray inspection system as defined by claim 13 wherein said fluoroscopic imaging means is mounted on the bottom surface of said support means and said optical coupling means comprises image reflector means located directly beneath said fluoroscopic imaging means.

16. The X-ray inspection system as defined by claim 15 wherein said exposure chamber includes a generally flat base located in said lower portion thereof and wherein said video camera means and said image reflector means are mounted on said base.

17. The X-ray inspection system as defined by claim 16 wherein said image reflector means comprises a prism or mirror.

18. The X-ray inspection system as defined by claim 13 and additionally including an X-ray tube tower mounted on said exposure chamber adjacent the upper portion thereof.

* * * * *